United States Patent
Friedman

(10) Patent No.: US 9,427,162 B2
(45) Date of Patent: Aug. 30, 2016

(54) DENTAL SHADE MATCHING METHOD AND DEVICE

(71) Applicant: Joshua Friedman, Ridgefield, CT (US)

(72) Inventor: Joshua Friedman, Ridgefield, CT (US)

( * ) Notice: Subject to any disclaimer, the term of this patent is extended or adjusted under 35 U.S.C. 154(b) by 97 days.

(21) Appl. No.: 14/076,617

(22) Filed: Nov. 11, 2013

(65) Prior Publication Data

US 2015/0173624 A1 Jun. 25, 2015

(51) Int. Cl.
*A61B 5/00* (2006.01)
*A61B 1/24* (2006.01)
*A61C 19/10* (2006.01)

(52) U.S. Cl.
CPC .............. *A61B 5/0088* (2013.01); *A61B 1/24* (2013.01); *A61B 5/0071* (2013.01); *A61B 5/0075* (2013.01); *A61C 19/10* (2013.01)

(58) Field of Classification Search
CPC .. A61C 19/10; A61B 5/0088; A61B 5/0071; A61B 5/0075; A61B 1/24
See application file for complete search history.

(56) References Cited

U.S. PATENT DOCUMENTS

| | | | | |
|---|---|---|---|---|
| 5,003,434 A | * | 3/1991 | Gonser | A61C 1/088 362/119 |
| 5,274,535 A | * | 12/1993 | Gonser | F21V 9/00 362/268 |
| 5,871,268 A | * | 2/1999 | Edens | G02B 6/0006 362/293 |
| 5,887,965 A | * | 3/1999 | Edens | G02B 6/0006 362/276 |
| 6,089,740 A | * | 7/2000 | Forehand | A61C 19/003 313/634 |
| 6,111,650 A | * | 8/2000 | Rawicz | G01J 3/02 356/402 |
| 6,501,542 B2 | * | 12/2002 | Jung | G01J 3/02 356/416 |
| 7,942,540 B2 | * | 5/2011 | Harbers | F21K 9/54 362/247 |
| 8,570,530 B2 | * | 10/2013 | Liang | A61B 1/00009 356/601 |
| 2003/0035107 A1 | * | 2/2003 | Overbeck | A61B 1/00052 356/405 |
| 2005/0014106 A1 | * | 1/2005 | Haisch | A61C 13/082 433/29 |
| 2005/0164144 A1 | * | 7/2005 | Streib | A61C 19/00 433/26 |
| 2005/0260536 A1 | * | 11/2005 | Costaras | A61C 19/10 433/26 |
| 2006/0285323 A1 | * | 12/2006 | Fowler | G01J 3/10 362/230 |
| 2007/0065769 A1 | * | 3/2007 | Rohner | A61C 1/0015 433/29 |
| 2007/0159818 A1 | * | 7/2007 | Rueggeberg | A61C 13/082 362/231 |
| 2008/0085111 A1 | * | 4/2008 | Fowler | A61B 1/00105 396/199 |

(Continued)

OTHER PUBLICATIONS

Rite lite 2 Tri-Spectra Shade Matching Light [Brochure] Addent, Inc. Danbury, CT. Sep. 2012.*

*Primary Examiner* — Cris L Rodriguez
*Assistant Examiner* — Hao D Mai

(57) ABSTRACT

The shade matching method and device of the subject invention is to be used by dentists and dental professionals to help in determining the correct shade of porcelain crowns, composite fillings and other cosmetically critical dental restorations. Based on the principle of metamerism, the method consists of using a light source for generating a light spectrum in at least two distinct wavelength spectra in sequence under the control of the operator of the light source inclusive of a first wavelength spectrum corresponding to daylight to enable the dentist or dental professional to perform a shade match the way a patient would view their restoration outside of a dental office in a real world environment and then switching to a second wavelength spectrum corresponding to either room light or ambient light.

6 Claims, 3 Drawing Sheets

(56) References Cited

U.S. PATENT DOCUMENTS

| | | | |
|---|---|---|---|
| 2008/0131836 A1* | 6/2008 | Rueggeberg | A61C 13/082 433/29 |
| 2008/0220396 A1* | 9/2008 | Sun | A61K 6/0052 433/228.1 |
| 2009/0068613 A1* | 3/2009 | Wang | A61C 19/066 433/29 |
| 2010/0062388 A1* | 3/2010 | Unsworth | F21V 21/40 433/29 |
| 2013/0101953 A1* | 4/2013 | Stone | F21V 29/004 433/29 |
| 2013/0244197 A1* | 9/2013 | Tjioe | G01J 3/0264 433/29 |
| 2015/0062957 A1* | 3/2015 | Bria | F21S 48/1394 362/555 |
| 2015/0228868 A1* | 8/2015 | Ouderkirck | H01L 25/0753 362/84 |

* cited by examiner

DENTAL SHADE MATCHING METHOD AND DEVICE

BACKGROUND

Dentists always try to match the shade of a restoration to an existing tooth in the patient's mouth. Historically, this takes place by bringing the patient to a nearby window using daylight as the light source. Literature suggests that the color temperature of 5500 degrees Kelvin be used as a standard light spectrum that represents light on a cloudy bright day at 12 o'clock noon.

Some current devices use florescent lamps or LED's to produce a standard light spectrum of 5500 Kelvin. However, when tooth shades are matched with the 5500 Kelvin light spectra there still remains a significant chance the restoration shade will not match the existing tooth shade under different lighting conditions. There are very expensive spectrophotometers that aid in tooth shade selection. These devices typically sell for more than ten times the cost of our invention. However, they only measure the tooth shade at one wavelength spectra.

For example, the dentist matches the shade at 5500 degrees Kelvin and it looks good in the dental office.

The patient goes home and looks at their restoration in their bathroom light which happens to be an incandescent lamp. They then call the doctor to say the shade "changed". This happens because what the doctor thought was a perfect match was only a good match but not perfect. In physics there is a principal called metamerism. Metamerism says that if a shade matches absolutely perfectly it should match in all color spectra, i.e., with all different light sources.

SUMMARY OF THE INVENTION

The shade matching method and device of the subject invention uses from 12 to 24 light emitting diodes (LED's) arranged in different groups each having a plurality of light emitting diodes (LED's) in a circular or rectangular array which is preferably concentric to one another. The preferred arrangement is two groups of an equal number of LED's in a circular array concentric to one another. For example, with just 12 LED's this device can produce three distinct color spectra to simulate different lighting conditions typically found in indoor and outdoor environments.

This method and device employs 12 to 24 LED's that can produce multiple wavelength spectra. By using 12 LED's our device produces three distinct wavelength spectra. A daylight color temperature of 5500 degrees Kelvin is typically seen in outdoors on a cloudy bright day. A warm white light of approximately 2800 to 3200 degrees Kelvin represents incandescent lighting typically seen in homes, restaurants and offices. An ambient light in the range of 3400 degrees Kelvin to 4200 degrees Kelvin is seen in mixed indoor environments where multiple light sources may be present. By turning on a set of 6-5500 degrees Kelvin LED's the device produces a daylight spectra. By turning on a set of 6-3200 degrees Kelvin the device produces lighting spectrum typical of an incandescent indoor environment. By turning on 12 LED's, 6 with 3200 degrees Kelvin and 6 with 5500 degrees Kelvin, the device produces a mixed ambient lighting spectrum of approximately 3900 degrees Kelvin.

DETAILED DESCRIPTION

Figure 1:
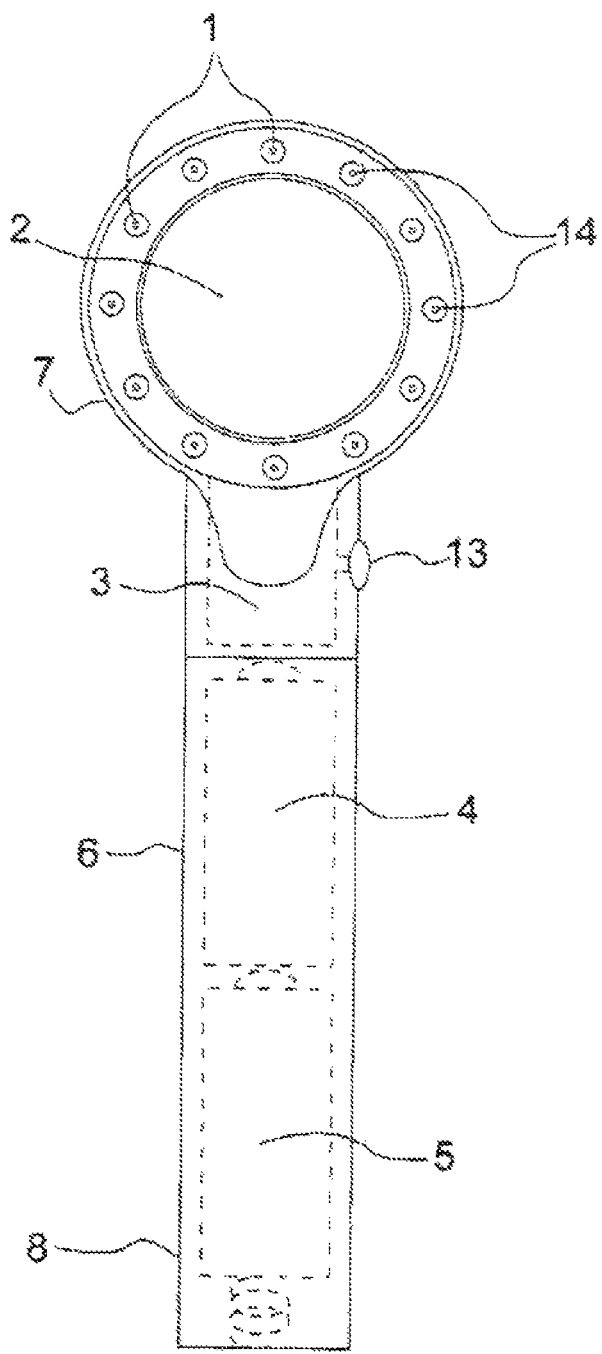
FIG. 1 is a front view of the device showing an array of 12 LED's in the head. The dotted lines show the internal batteries, a circuit board and on/off switch.
Figure 2:
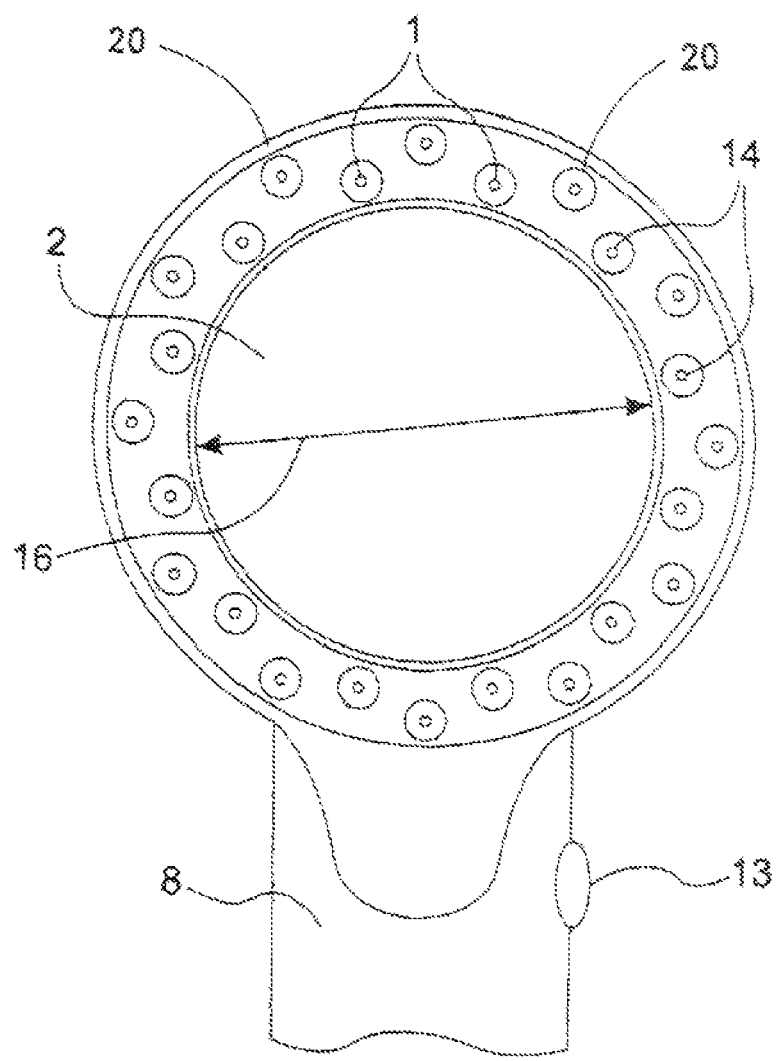
FIG. 2 shows an embodiment of the device of FIG. 1 using a 24 LED head and an on/off switch.

The shade matching device in the present invention is illustrated in FIG. 1 and FIG. 2. it is a simple battery operated hand held device that uses multiple color matched LED's.

FIG. 1 shows the housing 8 of a hand held device with a battery compartment 6 and batteries 4 and 5. The head contains a viewing opening 2. A circuit board 3 controls the operation and sequencing of the LED conditions. The switch 13 turns the unit on and off. The head 7 houses the rest of the circuit board 3 and provide electrical connection to the LED's. In this iteration using 12 LED's, the grouping of LED's 1 represents one wavelength spectra, for example 5500 degrees Kelvin. The grouping of LED's shown as 14, represents a second grouping of LED's for example, 3200 degrees Kelvin. The grouping of LED's shown as 14 represents a second grouping of LED's for example, 3200 degrees Kelvin. When both sets of LED's are on simultaneously, the combined wavelength spectra is 3900 degrees Kelvin.

FIG. 2 shows a preferred version of this invention using 24 LED's. This version of the invention provides for four or five wavelength spectra. For example, this arrangement would provide 6 LED's in the 360-440 nanometer range. The six LED's in the 360-440 nanometer range can be arranged in line with one of the other groups of LED's, or with 3 LED's in each of two groups of LED's or arranged as a third group concentric to the other groups. Energy in the 360-440 nanometer range covers long wave U.V. and short wavelength visible light. In this spectral range normal teeth fluoresce. When restorations are made it is important to use materials that replicate the natural fluorescence of teeth so they look life like in lighting conditions where a small amount of the U.V. light spectrum is present, i.e. —outdoors or in stage or film lighting where the high color temperature of the light source used produces near U.V. energy. By providing the dentist with what a tooth shade looks like when exposed to long wave U.V. light, the material, i.e., ceramic, porcelain or composite fluorescent effects can easily be observed. During the preparation of the restoration, i.e., crown can be then constructed to include small amounts of fluorescent material that will replicate the life like appearance of natural teeth. In this version of my invention the sequence of light spectra would be as follows. In using this method depress the switch 13, LED string 1 (5500 degree Kelvin) turns on. Next, depress the switch a second time and LED string 1 is off and LED string 14 (3200 degree Kelvin) turns on. Depress the switch 13 a third time and both string 1 and 14 go on simultaneously. When restorations are made from materials that do not fluoresce as real teeth do, they will typically appear very dark or black under U.V. illumination.

Depress switch 13 a fourth time, string 1 and 14 is off and string 20 (360-440 nanometers) turns on. Depress the switch 13 a fifth time and all LED's are off.

If desired, an additional light spectrum can be made available by configuring a different combination of the 24 LED on/off grouping.

Figure 3:
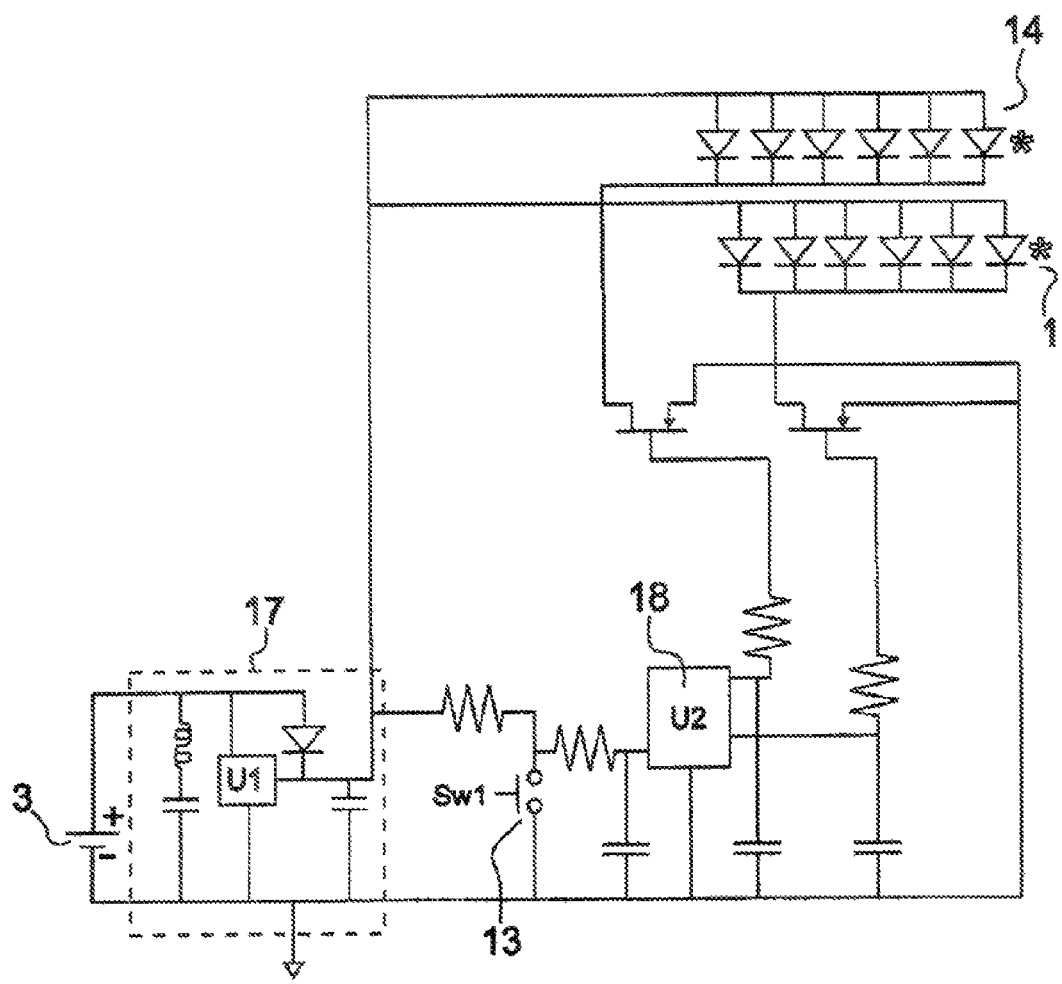
FIG. 3 is a circuit schematic diagram of the electronic circuit in the circuit board of FIG. 1 for controlling the switching sequence of different groups of LED's for producing different distinct light color spectra under the control of the operator of the device.

FIG. 3 shows a preferred electronic drive circuit for powering and controlling the functions of the LED's. The power supply is shown as 17, with a battery power source 3. Switch 13, can scroll though different combinations of LED wavelengths. The circuit contains a microprocessor 18, determines which LED's are on or off. It could also control additional LED's if desired. It should be understood that the angle of dispersion of each LED controls the focal distance of the generated light relative to the target dental restoration.

What is claimed:

1. A method for matching a color shade of a tooth or teeth for shade matching dentition comprising the steps of:
   directing a first light spectra onto a surface of a tooth or teeth, said first light spectra having a first wavelength spectra corresponding to daylight spectra at a color temperature of about 5500° K, and visually comparing a color shade of said tooth or teeth to a plurality of selected color shades from a standard shade matching guide;
   selecting a desired color shade from said plurality of selected color shades, said selected desired color shade substantially corresponds visually to the color shade of said tooth or teeth with said first light spectra directed thereon; and
   directing a second light spectra or a third light spectra onto said surface of said tooth or teeth by switching from said first light spectra to said second light spectra or said third light spectra, said second light spectra having a second wavelength spectra corresponding to room light at a color temperature in a range of about 2800° K to 3200° K, said third light spectra having a third wavelength spectra corresponding to ambient light at a color temperature in a range of about 3400° K to 4200° K, and verifying said selected desired color shade by visually comparing said selected desired color shade to said color shade of the tooth or teeth being treated with said second light spectra or said third light spectra directed thereon.

2. The method according to claim 1, wherein said third wavelength spectra corresponds to ambient light at a color temperature of about 3900° K.

3. The method according to claim 1, wherein each of said first, second, and third light spectra, is derived from a light source comprising a plurality of light emitting diodes arranged in groups, each of said groups of light emitting diodes generates a distinctly different wavelength spectra selected from said first, second, third wavelength spectra, and a fourth wavelength spectra in a range of 360-400 nanometer, the fourth wavelength spectra is used for checking for fluorescence of a restorative material.

4. The method according to claim 1, wherein the source of light is switched from one of said first, second, third, and fourth light spectra to another one of said first, second, third, and fourth light spectra in sequence under control of an operator of the source of light in a time period of less than about one minute.

5. The method according to claim 1 wherein said groups of light emitting diodes include at least a first group generating for said first light spectra, a second group generating said second light spectra, and wherein said third light spectra is generated by turning on said first group and said second group simultaneously.

6. The method according to claim 4 wherein the source of light is switched from one of said first, second, third, and fourth light spectra to another one of said first, second, third, and fourth light spectra in the sequence of said first, second, third, and then fourth light spectra.

* * * * *